US00PP23475P2

(12) United States Plant Patent
Bédard

(10) Patent No.: US PP23,475 P2
(45) Date of Patent: Mar. 19, 2013

(54) HYBRID TEA ROSE PLANT NAMED 'WEKMEMOLO'

(50) Latin Name: *Rosa hybrida*
Varietal Denomination: WEKmemolo

(75) Inventor: Christian Bédard, Brea, CA (US)

(73) Assignee: Weeks Roses, Pomona, CA (US)

( * ) Notice: Subject to any disclaimer, the term of this patent is extended or adjusted under 35 U.S.C. 154(b) by 0 days.

(21) Appl. No.: 13/373,017

(22) Filed: Nov. 2, 2011

(51) Int. Cl.
*A01H 5/00* (2006.01)

(52) U.S. Cl. ..... Plt./133

(58) Field of Classification Search ..... Plt./133
See application file for complete search history.

*Primary Examiner* — Annette Para

(74) *Attorney, Agent, or Firm* — McKee, Voorhees & Sease, P.L.C.

(57) ABSTRACT

A new variety of Hybrid Tea rose suitable for garden decoration, having flowers of pure white coloration.

1 Drawing Sheet

Classification: The present invention relates to a new *Rosa hybrida* plant.

Variety denomination: The new plant has the varietal denomination 'WEKmemolo'.

BACKGROUND OF THE INVENTION

This invention relates to a new and distinct variety of Hybrid Tea Rose. It has as its seed parent the variety known as 'WEKmeredoc' (not patented) and an undisseminated seedling of my creation as its pollen parent with the following genetic origin (Moonstone×Baby Love).

SUMMARY OF THE INVENTION

Among the features which distinguish the new variety from other presently available and commercial rose cultivars known to the inventor are the following combinations of characteristics: its strong spicy grapefruit and rose fragrance, its long and narrow sepals that leave a portion of the petals exposed even when the bud is closed and its predominance of stems with very few prickles. The plant has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmemolo' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKmeredoc' by the following combination of characteristics: whereas 'WEKmemolo' bears very double flowers (about 50 to 65 petals) of pure white coloration, 'WEKmeredoc' bears double flowers of light pink coloration with significantly lesser petalage (about 17 to 25 petals). The new variety has an upright medium height to somewhat tall growing habit (about 140 to about 180 cm. in height), whereas the seed parent has an upright moderately spreading significantly shorter growing habit (about 90 cm. in height).

The new variety may be distinguished from its pollen parent, an undisseminated seedling of my creation by the following combination of characteristics: whereas 'WEKmemolo' bears very double flowers (about 50 to 65 petals) of pure white coloration, the undisseminated seedling bears semi-double flowers of medium yellow coloration with significantly lesser petalage (about 12 to 17 petals). The new variety has an upright medium height to somewhat tall growing habit (about 140 to about 180 cm. in height), whereas the pollen parent has a bushy moderately spreading significantly shorter growing habit (about 100 to about 120 cm. in height).

COMPARISON WITH THE CLOSEST COMMERCIALLY AVAILABLE CULTIVAR

The new variety may be distinguished from its closest commercially available cultivar, 'MAClanoflan' (not patented) by the following combination of characteristics: whereas 'WEKmemolo' bears very double flowers (about 50 to 65 petals), 'MAClanoflan' bears double flowers with significantly lesser petalage (about 26 to 40 petals). The new variety has an upright medium height to somewhat tall growing habit (about 140 to about 180 cm. in height), whereas the closest commercially available cultivar has an upright significantly shorter growing habit (about 90 to about 150 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of October. Phenotypic expression may vary with environmental, cultural and climatic conditions, as well as differences in conditions of light and soil.

FLOWER

The new variety usually bears its flowers singly. Flowers are borne on strong long stems (about 62 to about 82 cm.). Outdoors, the plant blooms abundantly and nearly continuously during the growing season. The flowers have a strong spicy grapefruit and rose fragrance.

BUD

The peduncle is about 3.8 to about 5.8 cm. in length, of somewhat heavy caliper (about 0.3 to about 0.6 cm. in diameter), and usually erect. It is smooth, with few stipitate glands and hairs. Peduncle color is between 146B and 144A sometimes lightly suffused, especially on the side exposed to the sun, with between 187B and 183B.

Before the calyx breaks, the bud is about 1.7 to about 2.3 cm. in diameter at the widest point, about 2.2 to about 2.5 cm. in length, and ovoid to somewhat pointed in shape. The surface of the bud bears between 12 to 25 foliaceous appendages, few stipitate glands and hairs, sometimes with stout much cut foliaceous parts extending beyond the tip of the bud about ¾ or more of its length. Bud color is between 137C and 144A sometimes moderately suffused, especially on the side exposed to the sun, with between 187B and 183B.

The sepals are about 2.6 to about 5.0 cm. in length and about 0.7 to about 0.9 cm. in width at the widest point. The sepals are long and narrow leaving a portion of the petals exposed even when the bud is closed. The outer surface color of the sepal is between 137C and 144A sometimes moderately suffused, especially on the side exposed to the sun, with between 187B and 183B. The inner surface color of the sepal is near 138B broadly bordered by near 137B. After the sepals open, the inner surface color is sometimes lightly suffused, especially on the area exposed to the sun, with between 187B and 187C. The inner surface of the sepal is covered with fine wooly tomentum; sepal margins are lined with many stipitate glands and hairs.

The receptacle of the flower is of medium length (about 0.4 to about 0.6 cm.) and average in caliper (about 0.7 to about 0.9 cm. in diameter). The receptacle is urn-shaped in form. Its surface is smooth with some hairs and with moderately thin fleshy walls. The receptacle color is between 146B and 144A.

As the petals open (after the calyx breaks), the bud is about 2.2 to about 2.8 cm. in diameter at the widest point, about 2.8 to about 3.3 cm. in length, and moderately ovoid to somewhat globular in form. The color of the under surfaces of the newly opened petals is between 2D and 4D sometimes blushed with between 144A and 144B on the outermost petals and sometimes lightly edge with near 53D. There is no visible change in coloration at the point where the petal attaches. The color of the upper surfaces of the newly opened petals is between 2D and 4D sometimes blushed with between 144A and 144B on the outermost petals. At the point where the petal attaches, there is a small zone of between 2C and 3D.

BLOOM

When fully open, the bloom ranges from about 9.0 to about 15.6 cm. in diameter. Petalage is very double with about 50 to 65 petals and about 1 to 5 petaloids irregularly arranged. When partially open, the bloom form is moderately high centered to cupped, and the petals are somewhat tightly spiraled to cupped with petal edges moderately reflexed outward. When fully open, the bloom form is cupped and the petals are loosely cupped to somewhat undulated with petal edges moderately reflexed outward to somewhat rolled on the outer petals.

PETALS

The substance of the petals is moderately heavy and of somewhat thin thickness, with upper surfaces slightly satiny and under surfaces slightly shiny to matte. The petals are about 3.9 to about 5.8 cm. in length and about 2.6 to about 4.9 cm. in width at the widest point. Petal margins are entire.

The outer petals are obovate in shape with rounded apices and sometimes slightly notched with one notch.

The inner petals are oblanceolate to somewhat obovate in shape with rounded apices and sometimes slightly notched with one notch. Sometimes the innermost petals are lightly folded inward along the midrib.

Petaloids are about 1.8 to about 3.4 cm. in length and about 0.7 to about 2.2 cm. in width at the widest point. Petaloids are irregularly shaped somewhat oblanceolate to subulate with rounded apices.

NEWLY OPENED FLOWER

The under surface color of the outer, intermediate and inner petals is between 155D and 155B. At the point where the petal attaches, there is a small zone of between 2C and 3D. The upper surface color of the outer, intermediate and inner petals is between 4D and 155B. At the point where the petal attaches, there is a somewhat large zone of between 2C and 3D.

The under and upper surface colors of the petaloids are similar in coloration to the upper and under surfaces of the intermediate and inner petals.

The general tonality of the newly opened flower is between 4D and 155B.

THREE-DAY-OLD FLOWER

The under and upper surface color of the outer, intermediate and inner petals is between 155D and 155B. At the point where the petal attaches on the under surface, there is a small zone of lighter than 2D. At the point where the petal attaches on the upper surface, there is a somewhat large zone of lighter than 2D.

The under and upper surface colors of the petaloids are similar in coloration to the upper and under surfaces of the intermediate and inner petals.

The general tonality of the three-day-old flower is between 155D and 155B.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 35) and are arranged regularly about the pistils; a few are mixed with petaloids. The filaments are of medium to somewhat long length (about 0.4 to about 1.2 cm.) most with anthers. Filaments are between 4D and 2D in color sometimes very lightly suffused with lighter than 53D. The anthers are somewhat large for the class and all open approximately at the same time. Anther color when immature is near 22A on the external part and near 18C on the internal part. Anther color at maturity is near 166B on the external part and near 200A on the internal part. Pollen is somewhat sparse to moderate and between 11D and 13D in color.

FEMALE REPRODUCTIVE ORGANS

Pistils vary in number (average about 70). The styles are moderately even, somewhat long in length (about 0.7 to about 1.1 cm.), average in caliper and loosely separated. Stigma color is between 21D and 20B. Style color is between 150C and 154C usually heavily suffused with between 53B and 47A. Ovaries are usually all enclosed in the calyx.

Hips have not been observed on this variety when grown in Wasco, Calif.

FOLIAGE

The compound leaves are usually comprised of three to five leaflets and are borne abundantly. The five-leaflet leaves are about 9.2 to about 15.9 cm. in length and about 8.2 to about 12.9 cm. in width at the widest point, moderately crisp to leathery in texture, and glossy in finish on the upper side and matte in finish on the under side. The terminal leaflets are about 5.0 to about 8.1 cm. in length and about 3.0 to about 5.7 cm. in width at the widest point, shaped ovate to somewhat oval with moderately acuminate to somewhat acute apices and rounded to somewhat acute bases. Their margins are usually simply serrate.

The upper surface color of the mature leaf is between 137A and 139A. The under surface color of the mature leaf is between 147B and 138B. The upper surface color of the young leaf is between 146A and 146B, often moderately suffused with between 187B and 183A. The under surface color of the young leaf is between 138B and 146B, often moderately suffused with between 187B and 183A.

The rachis is moderately heavy in caliper and rough. The upper side is deeply grooved with few stipitate glands on the edges of the grooves. The under side of the rachis is rough with few stipitate glands and small prickles. The rachis color is near 146D on the under side and near 137B on the upper side often moderately suffused on the young leaf with between 187B and 183A.

The stipules are about 1.3 to about 1.6 cm. in length and moderately wide (about 0.6 to about 1.1 cm.) with somewhat long straight points that usually turn out at an angle of more than 45 degrees. The under and upper surface color of the stipule is between 137C and 138A.

The petiole is moderately heavy in caliper and rough. The upper side is deeply grooved with few stipitate glands on the edges of the grooves. The under side of the petiole is rough with few stipitate glands and small prickles. The petiole is about 0.5 to about 1.4 cm. in length and about 0.1 to about 0.3 cm in width at the widest point. The petiole color is near 146D on the under side and near 137B on the upper side often moderately suffused on the young leaf with between 187B and 183A.

The plant displays an above average degree of resistance to powdery mildew and rust as compared to other commercial varieties grown under comparable conditions in Wasco, Calif. The plant's winter hardiness and drought/heat tolerance are yet to be determined.

GROWTH

The plant has an upright medium height to somewhat tall growing habit (about 140 to about 180 cm. in height and about 70 to about 85 cm. spread at the widest point), with moderately full branching. It displays very vigorous growth and the canes are of medium to somewhat heavy caliper for the class (about 1.4 to about 2.4 cm. in diameter at the widest point).

The color of the major stems is between 147B and 146B. They bear some large prickles that are about 0.9 to about 1.4 cm. in length. The large prickles are almost straight to angled slightly downward with a medium length broad oval base; prickle color is between 165A and 200D often moderately suffused with near 199D. The major stem bears few small prickles of similar shape and coloration.

The color of the branches is between 146B and 144A sometimes very lightly suffused with near 187C. They bear very few large prickles which are of similar size and shape to the large prickles on the major stems; prickle color is between 160A and 161B sometimes lightly suffused with near 187D. The branches bear very few small prickles of similar shape and coloration.

The color of the new shoots is between 146C and 144A sometimes lightly suffused with between 187B and 183A. They bear no large or small prickles.

I claim:

1. A new and distinct Hybrid Tea rose plant of the variety substantially as described and illustrated herein.

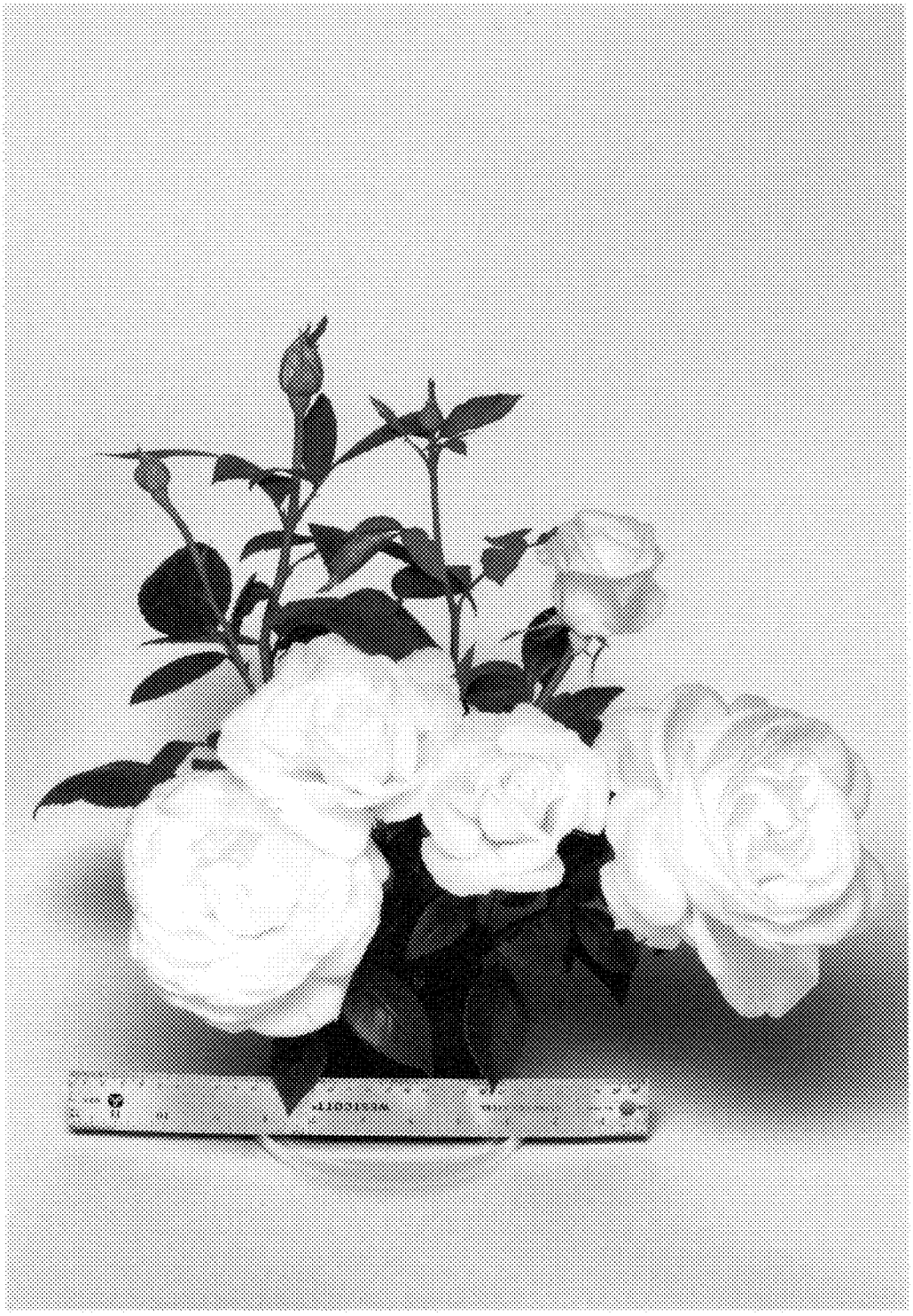

* * * * *